US011903857B2

United States Patent
Folan

(10) Patent No.: US 11,903,857 B2
(45) Date of Patent: Feb. 20, 2024

(54) ATRAUMATIC DELIVERY SYSTEM

(71) Applicant: Boston Scientific Scimed, Inc., Maple Grove, MN (US)

(72) Inventor: Martyn G Folan, Loughrea (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 360 days.

(21) Appl. No.: 17/130,864

(22) Filed: Dec. 22, 2020

(65) Prior Publication Data

US 2021/0236315 A1    Aug. 5, 2021

Related U.S. Application Data

(60) Provisional application No. 62/968,850, filed on Jan. 31, 2020.

(51) Int. Cl.
*A61F 2/966* (2013.01)
*A61F 2/95* (2013.01)

(52) U.S. Cl.
CPC ............ *A61F 2/966* (2013.01); *A61F 2/9517* (2020.05)

(58) Field of Classification Search
CPC .......... A61F 2/9527; A61F 2/966; A61F 2/95; A61F 2002/9505; A61F 2250/001; A61F 2250/0039; A61F 2250/0058; A61F 2250/0065

See application file for complete search history.

(56) References Cited

U.S. PATENT DOCUMENTS

| | | | | |
|---|---|---|---|---|
| 5,855,565 A | * | 1/1999 | Bar-Cohen | A61M 29/02 606/198 |
| 6,336,933 B1 | * | 1/2002 | Parodi | A61F 2/95 606/139 |
| 2012/0136426 A1 | * | 5/2012 | Phan | A61B 17/00234 623/1.12 |

(Continued)

FOREIGN PATENT DOCUMENTS

| WO | 2011084342 A1 | 4/2011 |
|---|---|---|
| WO | 2011084342 A1 | 7/2011 |

OTHER PUBLICATIONS

International Search Report and Written Opinion for the International Patent Application No. PCT/US2020/066623, dated Mar. 25, 2021, 12 pages.

(Continued)

*Primary Examiner* — Paul B Prebilic
(74) *Attorney, Agent, or Firm* — Seager, Tufte & Wickhem, LLP

(57) ABSTRACT

The present disclosure relates generally to the field of medical devices. In particular, the present disclosure relates to delivery systems configured to position a distal portion of a medical device within a restricted anatomical area. In one example, a delivery system may include a flexible elongate member with an inner member within a lumen of the flexible elongate member. A stent may be constrained therebetween. The stent may be configured to move between a first configuration to a second deployed configuration when unconstrained from the flexible elongate member. When the stent moves from the first configuration to the second configuration, the inner member may change from a first length to a second, shorter length. Other embodiments are contemplated.

8 Claims, 4 Drawing Sheets

(56) References Cited

U.S. PATENT DOCUMENTS

| | | | |
|---|---|---|---|
| 2016/0089132 A1* | 3/2016 | Butler | A61F 2/2487 |
| | | | 606/151 |
| 2017/0112647 A1* | 4/2017 | Sachar | A61F 2/966 |
| 2018/0271530 A1 | 9/2018 | Dayton et al. | |
| 2018/0361127 A1* | 12/2018 | Gray | A61B 17/11 |
| 2019/0125534 A1* | 5/2019 | Arcaro | A61F 2/2439 |
| 2019/0350645 A1* | 11/2019 | Montague | A61B 18/1482 |

OTHER PUBLICATIONS

Instructions for Use—Hanarostent® Biliary (NC)—BPD M.I. TECH—URL: http://www.mitech.co.kr/custom/prCustomView.do?disp_idx=DPIDX00012&menu_nix=7TA7vJOJ—publication dated Aug. 1, 2019.

\* cited by examiner

ATRAUMATIC DELIVERY SYSTEM

CROSS REFERENCE TO RELATED APPLICATIONS

This application claims the benefit of priority under 35 U.S.C. § 119 to U.S. Provisional Patent Application Ser. No. 62/968,850, filed on Jan. 31, 2020, which is incorporated by reference in its entirety for all purposes.

FIELD

The present disclosure relates generally to the field of medical devices. In particular, the present disclosure relates to medical device delivery systems.

BACKGROUND

Proper positioning and deployment of a distal flange of a self-expanding metal stent (SEMS) within an anatomical area (e.g., body lumen, passage, vessel, duct, etc.) requires sufficient space beyond a distal end of a delivery system. This is due, at least in part, to an elongated profile of the stent when loaded onto the delivery system (e.g., prior to deployment), foreshortening of the stent that occurs upon deployment of a distal flange, or obstruction by a portion of the delivery system that extends into an anatomical area. Anatomical areas that lack sufficient distal space (e.g., head space) may result in improper deployment of the distal flange due to improper alignment, kinking/bending of the delivery system, and/or perforation of the body lumen wall.

It is with these considerations in mind that the improvements of the present disclosure may be useful.

SUMMARY

Various embodiments described herein may include a device, a system, an apparatus, and a method, and so forth including a stent. A delivery system may comprise a flexible elongate member and an inner member slidably disposed within a lumen of the flexible elongate member. A delivery system may further include a stent loaded in a first constrained configuration between a distal portion of the flexible elongate member and a distal portion of the inner member, wherein the stent may be configured to move from the first constrained configuration to a second deployed configuration when unconstrained from the flexible elongate member. The distal portion of the inner member may be configured to move between a first length when disposed within the distal portion of the flexible elongate member and a second length when the stent is unconstrained from the flexible elongate member, and the first length may be greater than the second length. The inner member may transition between the first length and the second length as the stent is unconstrained, and the stent may be unconstrained from the flexible elongate member by moving one or both of the inner member and the flexible elongate member relative to one another. The delivery system may comprise a handle operatively attached to a proximal end of one or both of the flexible elongate member and the inner member, wherein the handle may be configured to move between a first position to proximally retract the flexible elongate member relative to the inner member and a second position to distally extend the flexible elongate member relative to the inner member. When the flexible elongate member is distally extended, the distal portion of the inner member may move from the second length to the first length. The distal portion of the inner member may have less lateral flexibility at the first length than at the second length. The distal portion of the inner member may include a plurality of loops, wherein a diameter of each loop at the first length, when the stent is in the first constrained configuration, may be less than its respective diameter at the second length, when the stent is in the second deployed configuration. The distal portion of the inner member may be disposed within a distal portion of the stent in the first constrained configuration, in the second deployed configuration, or in both. The distal portion of the inner member may be formed of a shape-memory material. The delivery system may comprise a penetrating element on a distal end of the inner member, the tissue penetrating element may be configured to form an opening in tissue. The tissue penetrating element may comprise an electrically conductive tip. The distal end of the inner member may comprise a compliant material that is more pliable than a proximal end of the inner member. In some embodiments described herein, an inner member of a stent delivery system may comprise an elongate shaft having a proximal end and a distal end and extending along a longitudinal axis. The proximal end may have a straight portion wherein the distal end may be configured to transition between a first configuration and a second configuration different than the first configuration such that in response to deployment from within the stent delivery system, the distal end may foreshorten from the first configuration to the second configuration. The distal end of the elongate shaft may be preformed in a plurality of loops, curls, waves, peaks and valleys, or combinations thereof, thereby forming the foreshortened configuration. The first configuration of the distal end of the elongate shaft may be constrained in a straightened configuration such that the distal end may have a first length of the first configuration extending along the longitudinal axis that is longer than a second length of the second configuration. The proximal end of the inner member may be substantially semi-rigid or rigid compared to a flexibility of the distal end of the elongate shaft. The distal end of the elongate shaft may be formed of a shape-memory material.

In one or more embodiments, a delivery system may comprise a flexible elongate member, an inner member may be slidably disposed within a lumen of the flexible elongate member, and a stent may be disposed in a first constrained configuration between a distal portion of the flexible elongate member and a distal portion of the inner member. In embodiments, the stent may be configured to move from the first constrained configuration to a second deployed configuration when unconstrained from the flexible elongate member. A distal portion of the inner member may include a first thickness and the remaining portion of the inner member may include a second thickness, and the first thickness may be less than the second thickness. The inner member may transition between a first length and a second length as the stent is unconstrained, and the stent may be unconstrained from the flexible elongate member by moving one or both of the inner member and the flexible elongate member relative to one another. The delivery system may comprise a handle operatively attached to a proximal end of the flexible elongate member, wherein the handle may be configured to move between a first position to proximally retract the flexible elongate member relative to the inner member and a second position to distally extend the flexible elongate member relative to the inner member. The distal portion of the inner member may be disposed within a distal portion of the stent in the first constrained configuration, in the second deployed configuration, or in both. The distal portion of the inner member may be formed of a shape-memory material. The delivery system may comprise a tissue penetrating element on a distal end of the inner member, and the tissue penetrating element may be configured to form an opening in tissue. The tissue penetrating element may comprise an electrically conductive tip.

According to one or more embodiments described herein, a method may include advancing a delivery system into a patient to position a distal end of the delivery system adjacent to a target tissue. A method may further include penetrating a wall of the target tissue to position a distal portion of the delivery system. In various embodiments, a method may include proximally retracting a flexible elongate member of the delivery system relative to an inner member of the delivery system extending within a lumen of the flexible elongate member, such that a distal portion of the inner member may move from a first length, when constrained within the lumen of the flexible elongate member, to a second length, when unconstrained from the flexible elongate member. A method may further comprise proximally retracting the delivery system relative to the target tissue and proximally retracting the flexible elongate member relative to the inner member. The target tissue may include a first body lumen and a second body lumen. The distal portion of the inner member may be pre-formed in a plurality of loops, curls, waves, peaks and valleys, or combinations thereof, and thereby may form a foreshortened configuration when unconstrained from the flexible elongate member.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to stent delivery systems, it should be appreciated that such delivery systems may be used to deliver a variety of medical devices (e.g., aneurysm coils, other implants, and the like, etc.) into a variety of restricted anatomical areas, including, but not limited to, body lumens (e.g., stomach, pancreato-biliary tree, colon, duodenum, jejunum, uterus, etc.), passages, vessels and/or ducts, to address a variety of conditions, beyond cyst or pseudocyst access and drainage. In examples, the stent could be placed for drainage, for access, to bridge one location to another across a space, or between apposed layers, as an anastomosis device, as a means to bypass a location, as a shunt, etc., and the like.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional or physician when introducing a device into a patient, while the term "proximal" refers to the end closest to the medical professional or physician when introducing a device into a patient.

Figure 1A:
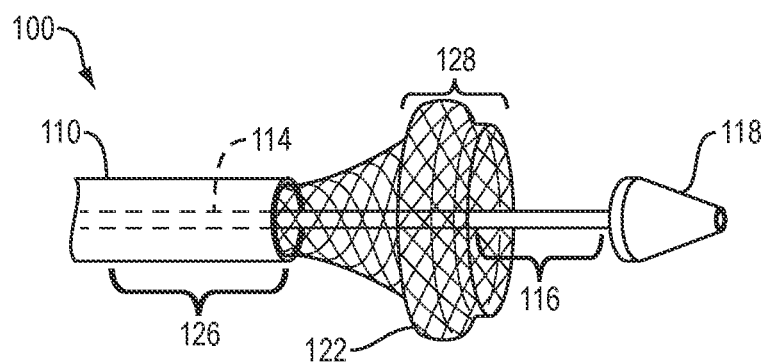
FIGS. 1A-1B provide perspective views of an illustrative stent delivery system.
Figure 1B:
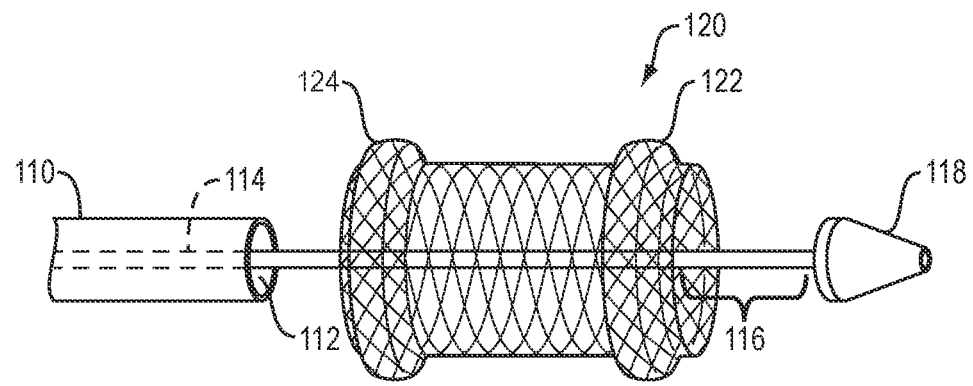

Referring to FIGS. 1A-1B, in one embodiment, a distal end of a delivery system 100 for delivering a stent 120 (e.g., a self-expanding stent such as Boston Scientific Corporation Axios™ Stent and Electrocautery Enhanced Delivery System) from a first body lumen into a second body lumen to facilitate drainage (e.g., transgastric or transduodenal drainage of a pancreatic pseudocyst or walled-off necrosis) may include an inner member 114 (e.g., wire, elongate shaft, etc.) slidably disposed within a lumen 112 of a flexible elongate member 110 (e.g., catheter, sheath, etc.) extending along a longitudinal axis. The stent 120 may be disposed in a first configuration (e.g., constrained or delivery configuration) within a distal end 126 of the flexible elongate member 110 and around a distal portion 116 of the inner member 114. In various embodiments, the stent 120 may include a self-expanding stent configured to move from the first configuration to a second configuration (e.g., unconstrained, expanded, or deployed configuration) when disposed beyond and/or unconstrained from the distal end 126 of the flexible elongate member 110. For example, a distal portion 128 of the stent 120 may radially expand outward from the longitudinal axis to form a distal flange 122 when unconstrained from the flexible elongate member 110 and a proximal portion of the stent may radially expand outward from the longitudinal axis to form a proximal flange 124 when disposed beyond the distal end of the flexible elongate member 110. A stent 120 may be unconstrained from the flexible elongate member 110 by moving one or both of the inner member 110 and the flexible elongate member 114 relative to one another. In various embodiments, a distal portion 116 of the inner member 114 may include the same size, shape, dimension(s) and/or material(s) as the remaining portion of the inner member 114, e.g., extending through the lumen 112 of the flexible elongate member 110. For example, the inner member 114, including the distal portion 116, may be formed from or otherwise include a substantially stiff and/or inflexible material that does not substantially bend/flex and/or change in length when unconstrained from the distal end of the flexible elongate member 110 (e.g., when the flexible elongate member 110 is proximally retracted to deploy the distal flange 122 of the stent 120 within a restricted anatomical area). In some embodiments, the distal portion 116 may be coupled to a tissue penetrating element 118.

In various embodiments, a handle (not shown) may be operatively attached to a proximal end of one or both of the flexible elongate member 110 and the inner member 114 and configured to move between a first position to proximally retract the flexible elongate member 110 relative to the inner member 114 (e.g., to deploy the distal and/or proximal flanges 122, 124 of the stent 120) and a second position to distally extend the flexible elongate member 110 relative to the inner member 114 (e.g., to restrain/re-sheath the distal and/or proximal flanges 122, 124 within the flexible elongate member 110). For example, a medical professional may re-sheath the distal flange 122 upon determining that the distal flange 122 is improperly positioned within the target body lumen, passage, duct or vessel.

Figure 2:
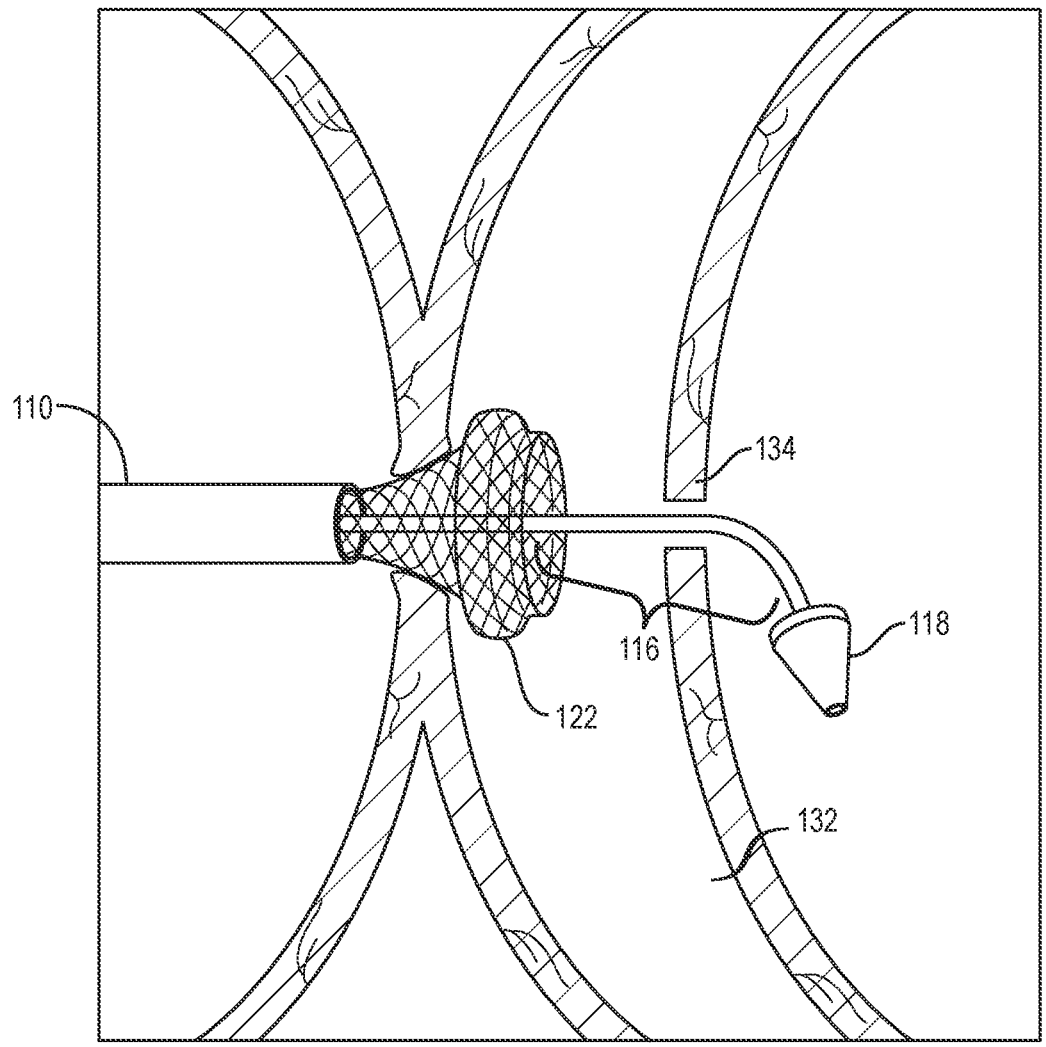
FIG. 2 provides perspective views of an exemplary stent deployment using the delivery system of FIGS. 1A-1B.

Referring to FIG. 2, in one embodiment, a delivery system 100 may be configured to deploy the distal flange 122 of the stent 120 in a constricted anatomical area 132 (e.g., the biliary tract). The distal portion 116 of the inner member 114 may extend beyond the deployed distal flange 122. An opposite wall 134 of the body lumen, or another obstruction, may not allow sufficient space in the body lumen to accommodate the distal portion 116 of the inner member 114. Accordingly, the distal portion 116 of the inner member 114 may kink or bend such that the distal flange 122 of the stent 120 may be misaligned and/or improperly deployed. In addition, or alternatively, the distal portion 116 of the inner member 114 may traumatically contact and/or perforate the opposite wall 134 of the body lumen.

Figure 3A:
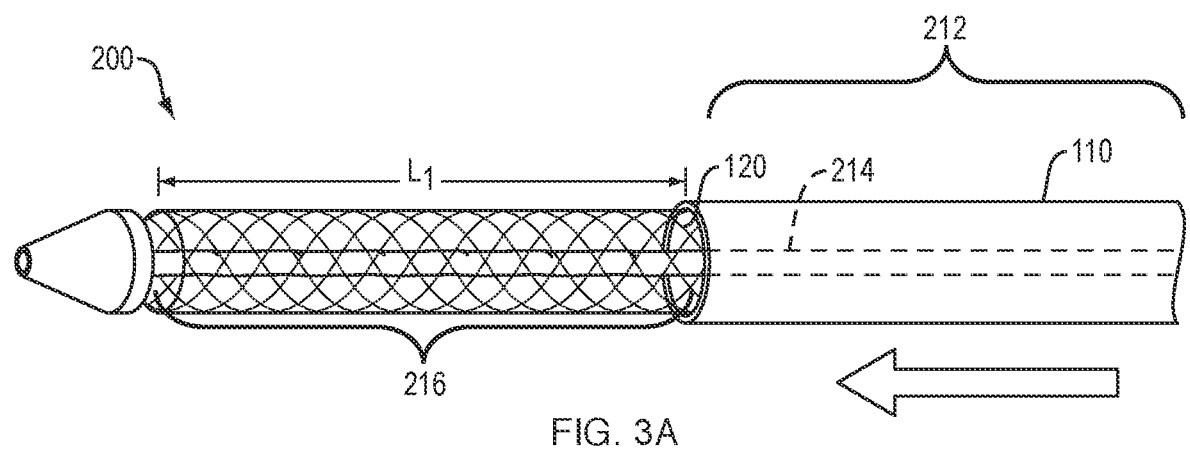
FIGS. 3A-3B provide perspective views of a stent delivery system, according to one embodiment of the present disclosure.
Figure 3B:
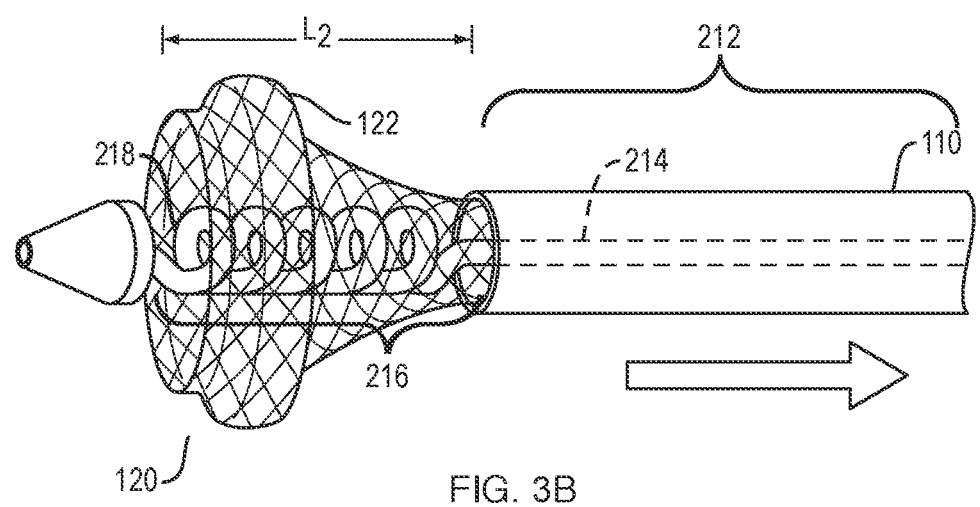

Referring to FIGS. 3A-3B, in one exemplary embodiment, a stent delivery system 200 of the present disclosure may include the same or similar elements as stent delivery system 100, but may include an inner member 214, instead of inner member 114, with a distal portion 216 configured to move between a first length ($L_1$) along a longitudinal axis when disposed within the distal portion of the flexible elongate member 110 (FIG. 3A) and a second length ($L_2$) along the longitudinal axis shorter than the first length when unconstrained from the distal end of the flexible elongate member 110 (FIG. 3B). The second length ($L_2$) may be sufficiently shorter than the first length ($L_1$) for the inner member to avoid traumatic interference with a wall of the body lumen or other obstruction. Additionally, or alternatively, the second length $L_2$ may be of a sufficiently short length to minimize or avoid contact with a body lumen wall or obstruction, or with the delivery system 200, so as not to interfere with the positioning of distal flange 122 of stent 120. In many embodiments, a second length $L_2$ may be configured to correspond with the foreshortening of a stent upon deployment from a sheath. For example, a stent with a saddle length 10 mm in length may be expected to have a saddle length of 14 mm when constrained about an inner member. The corresponding inner member may then be designed to have a first length $L_1$ of 14 mm and a second length $L_2$ of 10 mm. When referring to the "saddle length" of stent, the length may refer to the length of the stent between two retention members (e.g., flanges) in the deployed configuration. Depending on how the retention members are arranged, this length may coincide with the overall length of the stent in the deployed configuration if the stents ends coincide with the position of the retention members. In other embodiments, the retention members may overhang the body of the stent, in which case the saddle length may be measured from the beginning of the retention members where they meet the body of the stent or the saddle length may be considered the distance between them at a point along the retention members where they are closest to each other. In some embodiments, the saddle length may be measured for a deployed configuration that represents the configuration deployed off of the delivery member and in other cases represents the configuration when deployed in or across tissue. Such lengths may be the same or differ. In many embodiments, a first length $L_1$ may be up to about 40% longer than a second length $L_2$. Thus, if the length of the saddle of the stent in a deployed configuration (second length $L_2$) is approximately 8 mm, 10 mm, 15 mm, 20 mm, 30 mm, or any other selected length, the first length $L_1$, or the constrained length, may be approximately 40% longer than the respective 8 mm, 10 mm, 15 mm, 20 mm, 30 mm, or any other selected length. The percentage degree of shortening between the first and second lengths may depend on the percentage degree of foreshortening desired or applicable for the corresponding stent being delivered, and/or the restricted space of or obstructions in the anatomy into which the stent is being delivered.

In many embodiments, a proximal portion 212 of an inner member 214 may comprise a straight portion. The distal portion 216 of the inner member 214 may include a plurality of curls or loops 218, although the shapes of the distal portion 216 are not so limited and may be formed into any sine waves, peaks and valleys, or other configuration that may shorten the distal portion 216. In some embodiments, the distal portion 216 may include any combination of curls, loops, waves, or peaks and valleys. In some embodiments, the distal portion 216 may be heat-set/pre-formed to include curls or loops 218, waves, peaks and valleys, or any combination thereof when in a relaxed position. The loops 218 may have a helical arrangement and/or a spring-like nature, such that they are elastically deformable. For example, at least the distal portion 216 may be formed of a shape-memory material such as Nitinol. The distal portion 216 may be constrained in a straightened configuration prior to deployment. In response to deployment from within the delivery system, the curls or loops 218 may be expandable to their heat-set/pre-formed shape such that the distal portion 216 is foreshortened. In some embodiments, the inner member 214 may be formed of a single material (e.g., shape-memory material), such that only the distal portion 216 may be heat-set/pre-formed in a non-straight configuration while the proximal portion 212 is heat-set in a straight configuration. In other embodiments, the proximal portion 212 may be formed of a material different than the distal portion. For example, the proximal portion 212 may be formed of a substantially semi-rigid or rigid material, and the distal portion 216 may be formed of a more flexible shape-memory material. The distal portion 216 may be connected to the proximal portion 212 by any of welding, soldering, brazing, adhesive, mechanical fasteners and the like.

A stent 120 in the first configuration may be disposed between the flexible elongate member 110 and the inner member 214. The lumen of the stent 120 in the first configuration may have a smaller diameter than the loops 218 in a relaxed position, such that the stent 120 in the first configuration applies a radial inward/compressive force on the loops 218. As a result, the loops 218 may be collapsed, compressed, or otherwise deformed when the stent 120 is in the first configuration.

In some embodiments, the stent 120 may have an outer diameter greater in a relaxed position than the diameter of the lumen of the flexible elongate member 110. The first configuration of the stent 120 within the flexible elongate member 110 may result in a radially inward/compressive force on the stent 120, which may be elastically deformable. For example, the stent 120 may have a slimmer profile and/or a compressed shape when in the first configuration as opposed to a second configuration. In some embodiments, the radially inward/compressive force of a flexible elongate member 110 on a stent 120 may be transferred to an inner member 214 disposed within the stent 120 in the first configuration. In other words, the stent 120 may apply a radially inward/compressive force on the inner member 214 disposed therein in the first configuration. The radially inward/compressive force of a flexible elongate member 110 on a stent 120 may cause the stent 120 to apply a radially inward/compressive force on loops 218 of an inner member 214 disposed therein in the first configuration.

Radially compressive force on the loops may constrain the loops 218 to a substantially linear configuration (e.g., the curls or loops 218 are constrained to be small, compressed, or linearly stretched; FIG. 3A). In embodiments, the inner member 214 may be sheathed within the flexible elongate member 110 and held in tension such that the distal portion 216 is held in a first, straightened configuration. In response to retraction of the flexible elongate member 110, the distal portion 216 may form into a pre-formed/heat-set shape, such as loops 216, as a second, relaxed configuration. In other words, as the stent 120 is deployed the distal portion 216 may foreshorten. This may be advantageous when a medical professional desires to deploy a stent 120 in a confined anatomical space or desires to avoid anatomical obstructions, or both. The first configuration of the flexible elongate member 110, the stent 120, and the inner member 214 may include lower levels of free volume and/or higher levels of stress, strain, and/or tension in the system. As a result, the arrangement may contribute to a higher stiffness than would be achieved by at least the inner member 214 alone. In some embodiments, the arrangement of the flexible elongate member 110, the stent 120, and the inner member 214 in the first configuration may be stiffer to allow the arrangement to be inserted through the scope and maneuvered into position as a more rigid column than is desired when deploying the stent 120. Accordingly, the arrangement of features in the present disclosure may enable a flexible elongate member 110 and/or inner member 214 with a thinner overall diameter to be used than in conventional systems while maintaining comparable and/or greater stiffness to respective components in the conventional systems.

In some embodiments, the flexible elongate member 110 may be retracted with respect to the inner member 214, causing the stent 120 to be unconstrained from the distal end of the flexible elongate member 110. When the stent 120 is unconstrained from the distal end of the flexible elongate member 110 (e.g. by proximally retracting the flexible elongate member 110 along the longitudinal axis), the distal portion of the stent 120 may radially expand to form a distal flange 122 (as described above) thereby releasing the radially inward/compressive forces exerted on the distal portion 216 of the inner member 214. The inner member 214 may accordingly change shape, for example, to a shape set by shape memory. The loops 218 may move from the substantially linear/smaller diameter configuration (FIG. 3A) to a curled, larger diameter configuration (FIG. 3B), thereby decreasing the length of (e.g., foreshortening) the distal portion 216 of the inner member 214. For example, the distal portion 216 may transition from a first length $L_1$ (FIG. 3A) to a second length $L_2$ (FIG. 3B). The inner member 214 may additionally, or alternatively, be less stiff in the second configuration than in the first configuration.

In some embodiments, a flexible elongate member 110 may be distally advanced with respect to the inner member 214, causing a deployed and/or partially deployed stent 120 to be reconstrained and/or recaptured by the distal end of the flexible elongate member 110. When the stent 120 is reconstrained by the distal end of the flexible elongate member 110 (e.g., by distally extending the flexible elongate member 110 along the longitudinal axis), the distal portion of the stent 120 may radially contract from a distal flange 122 to a compressed configuration. The stent 120 may accordingly exert radially inward/compressive forces on the distal portion 216 of the inner member 214. The inner member 214 may accordingly change shape, for example, from a shape set by shape memory to a first constrained configuration. For example, the loops 218 may move from a curled, larger diameter configuration (FIG. 4B) to a substantially linear/smaller diameter configuration (FIG. 3A), thereby increasing the length of (e.g., extending) the distal portion 216 of the inner member 214. For example, the distal portion 216 may transition from a second length $L_2$ (FIG. 3B) to a first length $L_1$ (FIG. 3A). Recapture of a stent 120 may enable reorientation and proper redeployment of the stent 120 in the case of improper alignment.

Design attributes for the inner member 214 may be tuned to provide desirable characteristics. For example, an inner member 214 may be designed to move from a pre-determined first length (e.g., $L_1$) to a pre-determined second length (e.g., $L_2$) different from the first length, to have a pre-determined stiffness in the first configuration, or to have a pre-determined flexibility in the second configuration. Design attributes may also include one or any combination of material and/or dimensional specifications such as length, shape, thickness, material, coil density, or mechanical, thermal, or chemical treatment as known in the art.

In some embodiments, an inner member 214 may have a lumen therethrough. The lumen may contain a guidewire, or a guidewire may be otherwise coupled to an inner member 214. The inner member 214 may constrain the guidewire. The guidewire may have a linear shape but deform to accommodate the shape of the inner member 214 as the inner member 214 changes shape. For example, the guidewire may adapt curls as the loops 218 of the inner member 214 expand with the transition of the stent 120 from the first configuration to the second configuration. The guidewire's change in shape may result in a change in length of the guidewire, where the change in length corresponds to the change of length of the inner member 214, such as from the first length $L_1$ to the second length $L_2$.

Figure 4:
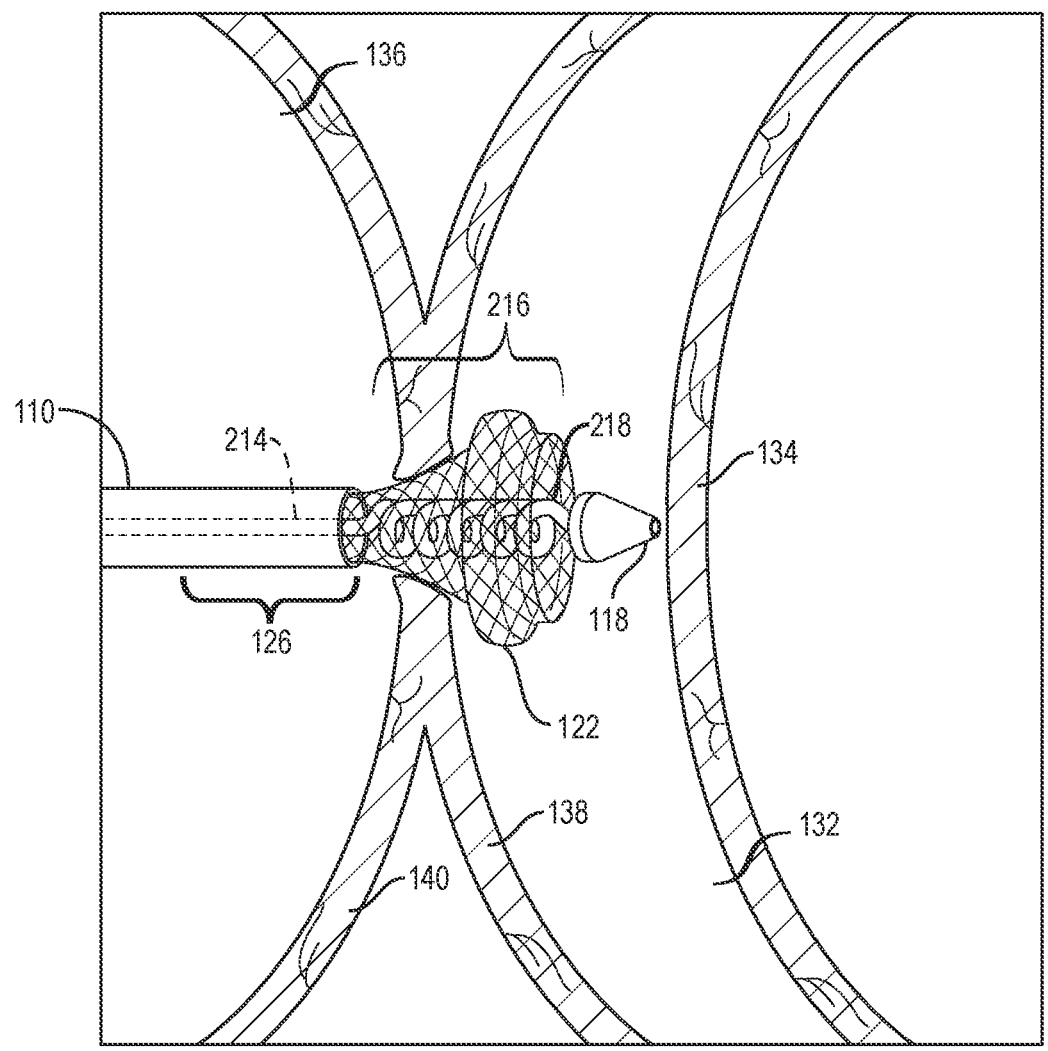
FIG. 4 provides a perspective view of an exemplary stent deployment using the delivery system of FIGS. 3A-3B.

Regarding FIG. 4, by way of comparison to FIG. 2, for example, the inner member 214 may deform upon deployment of the distal flange 122 to minimize or prevent contact with the opposite wall 134 of a restricted anatomical area 132. For example, the inner member 214 may form loops 218 in a foreshortened length to avoid potential traumatic contact of a tissue penetrating element 118 with the opposite wall. Similarly, the distal portion 216 may deform and atraumatically contact the opposite wall of the restricted anatomical area to minimize the risk of perforation. Mechanical characteristics of the inner member 214 may change with the deformation. For example, the inner member 214 may have higher lateral flexibility after deformation, allowing it to avoid traumatic contact with the opposite wall of the restricted anatomical area.

In various embodiments, the flexible elongate member 110 may be distally extended over the partially deployed stent 120 so that the stent 120 is partially or entirely re-constrained, or re-sheathed. In some embodiments, the flexible elongate member 110 may, as extended, exert radially inward/compressive forces onto the stent. As a result, the stent may be confined by an inner surface of the flexible elongate member 110 to be partially or entirely recaptured.

Additionally, or alternatively, the flexible elongate member 110 and/or the stent may exert radially inward/compressive forces onto the inner member 214 as the flexible elongate member 110 is distally extended. The inner member 214 may change shape so as to cause the loops 218 to move from the larger diameter configuration (FIG. 3B) to the substantially linear/smaller diameter configuration (FIG. 3A). Accordingly, the inner member may move from a shorter length (such as $L_2$) to a longer length (such as $L_1$).

In various additional embodiments, the distal portion 216 of the inner member 214 may include an outer dimension (e.g., thickness, diameter, etc.) that is less than a corresponding outer dimension of the remaining portion of the inner member 214. The distal portion 216 may accordingly deform or bend (e.g., foreshorten) more easily than the remaining portion of the inner member 214 upon deployment of the distal flange 122 to minimize or prevent contact with the opposite wall 134 of the restricted anatomical area 132. For example, the distal portion 216 may be more flexible than the remaining portion of the inner member 214 according to its relatively smaller diameter. Similarly, the relatively thinner/more flexible distal portion 216 may deform and atraumatically contact the opposite wall 134 of the restricted anatomical area 132 to minimize the risk of perforation. In addition, or alternatively, the distal portion 216 of the inner member 214 may include a different material (e.g., a more flexible and/or pliable material) than the remaining portion of the inner member to facilitate atraumatic contact with the opposite wall 134 of the restricted anatomical area 132.

In use and by way of example, a stent delivery system 200 of the present disclosure may be advanced through a body passage of a patient to position a distal end of the delivery system 200 adjacent to a wall of a first body lumen 136 (e.g., a stomach). The stent delivery system may then be distally advanced such that a tissue penetrating element 118 (e.g., sharpened and/or electrically conductive tip, etc.) disposed on a distal end of the inner member 214 may create an opening in a target tissue. A target tissue may comprise one or more walls, lumens, or other structures in a body. For example, a target tissue may include a first body lumen 136 and a second body lumen (e.g., restricted anatomical area 132). At least one wall in the target tissue may correspond with the first body lumen and/or the second body lumen. For example, tissue walls such as opposite wall 134 and second tissue layer 138 may correspond with restricted anatomical area 132, and first tissue layer 140 may correspond with first body lumen 136. In many embodiments, a target tissue may be adjacent to at least one body lumen. For example, tissue walls such as opposite wall 134 and second tissue layer 138 may be target tissues respectively adjacent to restricted anatomical area 132 and first body lumen 136. The stent delivery system may be distally advanced to position a distal portion of the flexible elongate member in the target tissue. In various embodiments, the restricted anatomical area may be adherent or non-adherent to the first body lumen. For example, a target tissue may separate the restricted anatomical area from the first body lumen.

The flexible elongate member 110 may then be proximally retracted such that a distal flange 122 of a stent 120 is deployed within the second body lumen of the target tissue (e.g., restricted anatomical area 132) and the distal portion 216 of the inner member 214 transitions from a first length to a second length (e.g., foreshorten as the loops 218 are formed). The distal flange 122 may thus be apposed to a second tissue layer 138 corresponding to the second body lumen. After the distal flange of the stent 120 is deployed, the stent delivery system 200 may then be proximally retracted to position the distal end 126 of flexible elongate member 110 in the second body lumen. If the distal end 126 of the flexible elongate member 110 is positioned incorrectly, the flexible elongate member 110 may be distally extended such that the distal flange 122 is re-constrained, with the distal portion 216 of the inner member 214 moving from the second length to a longer length, such as the first length. Once the distal end 126 of the flexible elongate member 110 has been properly re-positioned in the second body lumen and the distal flange 122 has been properly deployed, the stent delivery system 200 may then be proximally retracted to position the proximal end of flexible elongate member 110 in the first body lumen and the flexible elongate member 110 may then be proximally retracted to deploy the proximal flange within the first body lumen. Accordingly, the proximal flange may be apposed to a first tissue layer 140 corresponding with the first body lumen. The stent delivery system 200 may then be removed from within the patient.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A delivery system, comprising:
    a flexible elongate member;
    an inner member slidably disposed within a lumen of the flexible elongate member, a distal portion of the inner member comprising a shape memory material;
    a stent loaded in a first constrained configuration between a distal portion of the flexible elongate member and a distal portion of the inner member; and
    a tissue penetrating element on the distal portion of the inner member, the tissue penetrating element configured to form an opening in tissue,
    wherein the stent is configured to move from the first constrained configuration to a second deployed configuration when unconstrained from the flexible elongate member; and
    wherein the shape memory material is configured to form into a plurality of preformed loops, curls, waves, or peaks and valley to foreshorten the inner member from a first length when disposed within the distal portion of the flexible elongate member to a second length when the stent is unconstrained from the flexible elongate member, the first length being greater than the second length.

2. The delivery system of claim 1, wherein the inner member transitions between the first length and the second length as the stent is unconstrained, and wherein the stent is unconstrained from the flexible elongate member by moving one or both of the inner member and the flexible elongate member relative to one another.

3. The delivery system of claim 1, further comprising a handle operatively attached to a proximal end of one or both of the flexible elongate member and the inner member, wherein the handle is configured to move between a first position to proximally retract the flexible elongate member relative to the inner member, and a second position to distally extend the flexible elongate member relative to the inner member.

4. The delivery system of claim 3, wherein, when the flexible elongate member is distally extended, the distal portion of the inner member moves from the second length to the first length.

5. The delivery system of claim 1, wherein the distal portion of the inner member includes a plurality of loops, and wherein a diameter of each loop at the first length, when the stent is in the first constrained configuration, is less than its respective diameter at the second length, when the stent is in the second deployed configuration.

6. The delivery system of claim 1, wherein the distal portion of the inner member is disposed within a distal portion of the stent in the first constrained configuration, in the second deployed configuration, or in both.

7. The delivery system of claim 1, wherein the distal portion of the inner member is formed of a shape-memory material.

8. The delivery system of claim 1, wherein the tissue penetrating element comprises an electrically conductive tip.

\* \* \* \* \*